United States Patent [19]

Shahin

[11] Patent Number: 4,634,674
[45] Date of Patent: Jan. 6, 1987

[54] PLANT REGENERATION FROM PROTOPLASTS

[75] Inventor: Elias A. Shahin, Moraga, Calif.

[73] Assignee: Atlantic Richfield Company, Los Angeles, Calif.

[21] Appl. No.: 478,955

[22] Filed: Mar. 25, 1983

[51] Int. Cl.$^4$ .................. A01B 79/00; C12N 5/00; C12N 5/02

[52] U.S. Cl. ...................... 435/240; 435/241; 435/948; 47/58; 935/91

[58] Field of Search .............. 435/240, 241, 948, 68; 47/58

[56] References Cited

U.S. PATENT DOCUMENTS 3,832,801  9/1974  Carlson et al. .................. 47/58

OTHER PUBLICATIONS

Zapata et al., *Theor. Appl. Genet.* vol. 59, pp. 265-268, 1981, "Somatic Embryogenesis from *Lysopersicon peruvianum* Leaf Mesophyll Protoplasts".

Zapata et al., *Plant Sci. Lett.* vol. 8, (1979) pp. 119-127, "The Effect of Temperature on the Division of Leaf . . .".

Cassells et al., *Phys. Plant,* vol. 42, pp. 236-242, 1978, "A Method for the Isolation of Stable Mesophyll Protoplasts from Tomato Leaves Throughout the Year Under Standard Conditions".

Scott, K. J. et al., *Proceedings of Symp. on Plant Tissue Culture,* 1978, "Isolation and Culture of Cereal Protoplasts", pp. 325-330.

Wen-an et al., *Proc. of Symp. on Plant Tissue Culture,* 1978, "Regeneration of Whole Plants from Tobacco Leaf Protoplasts", pp. 293-315.

Barz et al., *Proc. of 1st Int. Cong. on Medicinal Plant Res.,* Sep. 1976, "Plant Tissue Culture and Its Bio-technological Application", pp. 316-322.

Zapata et al., Plant Science Letters, vol. 23, pp. 41-46, 1981, "Callus Formation from Leaf Mesophyll Protoplasts of Three Lycopersicom Species".

Shahin, E. A. and Shepard, J. F., "Cassava Mesophyll Protoplasts: Isolation, Proliferation, and Shoot Formation," *Plant Science Letters,* 17 (1980), pp. 459-465.

Meredith, Carole P., "Selection and Characterization of Aluminum-Resistant Variants From Tomato Cell Cultures," *Plant Science Letters,* 12 (1978) pp. 25-34.

Cassells, A. C., "Uptake of Charged Lipid Vesicles by Isolated Tomato Protoplasts," *Nature,* 275 (1978) p. 760.

Padmanabhan, Vasantha et al., "Plantlet Formation from *Lycopersicon esculentum* Leaf Callus," *Can. J. Bot.,* 52 (1974) pp. 1429-1432.

Meredith, Carole P., "Response of Cultured Tomato Cells to Aluminum," *Plant Science Letters,* 12 (1978) pp. 17-24.

Ellis, B. E., "Non-Differential Sensitivity to the Herbicide Metribuzin in Tomato Cell Suspension Cultures," *Canadian Journal of Plant Science,* 58 (1978), pp. 775-778.

Kalil, Millicent L. & Hildebrandt, Albert C., "Effects of Agrobacterium sp. on Cell Cultures of Tomato," φyton, 28(2), (1971), pp. 177-186.

Pojnar, E., Willison, J. H. M. and Cocking, E. C., "Cell-Wall Regeneration by Isolated Tomato-Fruit Protoplasts," *Protoplasma,* 64 (1969), p. 460.

Coleman, Warren K. et al., "Promotion of Root Initiation by Gibberellic Acid in Leaf Discs of Tomato (*Lycopersicon esculentum*) Cultured In Vitro," *New Phytol.* 78 (1977) pp. 47-54.

De Wit, Pierre J. G. M., "Isolation and Culture of Tomato Mesophyll Protoplasts," *Acta. Bot. Neerl.,* 25(6) (1976) pp. 475-480.

"The Race to Breed a 'Supertomato'," *Business Week,* Jan. 10, 1983, pp. 33, 37.

Shepard, James F., "The Regeneration of Potato Plants from Leaf-Cell Protoplasts," *Scientific American,* 246 (1982), pp. 154-166.

Hanson, Maureen R., "Cell and Tissue Culture of Lycopersicon", *Plant Tissue Culture* (1982), pp. 193-194.

*Primary Examiner*—Thomas G. Wiseman
*Assistant Examiner*—Robin Lyn Teskin
*Attorney, Agent, or Firm*—Craig E. Larson

[57] ABSTRACT

A method is provided for the regeneration of cultivated tomato plants from protoplasts. The protoplasts are extracted from a donating plant which has been substantially isolated from its source of endogenous hormones and grown in an artificial medium which is substantially hormone-free, and thereafter cultured in substantially similar media to form callused cell colonies and shoots which are similarly grown to form rooted, mature plants.

46 Claims, 7 Drawing Figures

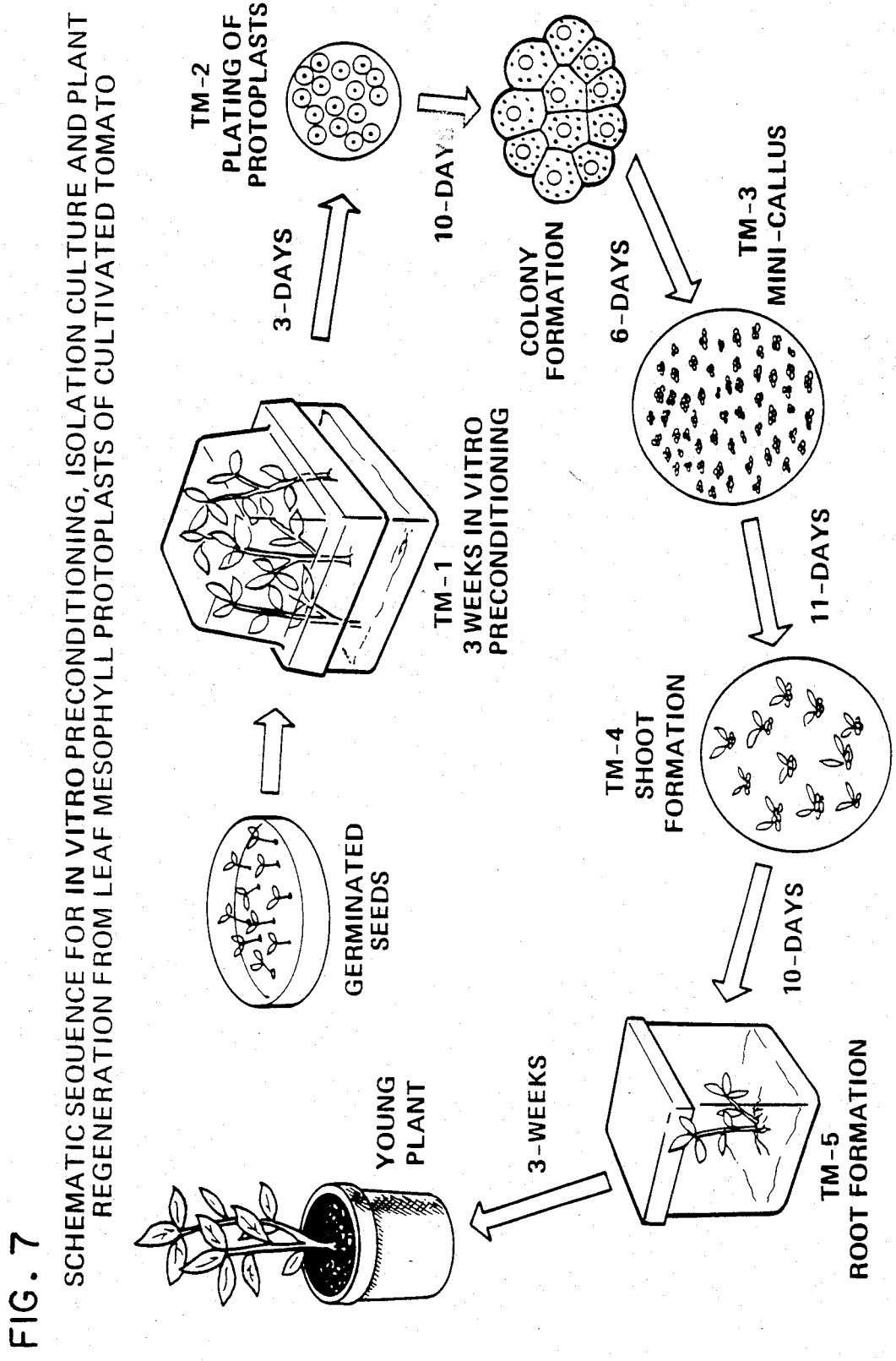
FIG. 7 SCHEMATIC SEQUENCE FOR IN VITRO PRECONDITIONING, ISOLATION CULTURE AND PLANT REGENERATION FROM LEAF MESOPHYLL PROTOPLASTS OF CULTIVATED TOMATO

PLANT REGENERATION FROM PROTOPLASTS

FIELD OF THE INVENTION

The field of art to which the invention pertains includes the field of the plant sciences, and particularly relates to the isolation and culturing of protoplasts and the regeneration of plants therefrom.

BACKGROUND AND SUMMARY OF THE INVENTION

Workers in the plant sciences have developed techniques for removing the rigid, cellulose wall of plant cells in order to obtain wall-less cells commonly known as protoplasts. Plant protoplasts have potential economic value in that they permit plant scientists to apply microbiological techniques for the production of improved plant varieties significant in agriculture. Thus, by taking advantage of naturally occurring variation or variation induced artifically by chemicals or radiation in the protoplasts, plant scientists may be able to select out plants bearing agriculturally useful new traits. The significant new advantage presented by plant protoplasts is that each single celled protoplast is theoretically capable of giving rise to a whole plant and subsequently to a new type of crop. Consequently, by the application of standard microbiological techniques, plant scientists may be able to deal with vastly more plants than ever before possible and therefore to detect much more readily the very rare events which lead to useful new varieties.

In addition plant protoplasts have considerable potential value in the production of hybrids, i.e. offspring from two different plant varieties, species or genera, which have important commercial value in agriculture. Protoplasts of different plant species may be fused to form a hybrid protoplast which is potentially capable of growing into a hybrid plant even in instances where the hybrid may be unobtainable because of genetic barriers using conventional plant breeding techniques.

Plant protoplasts are expected to be the point of attack for manipulation of the plant genome using recombinant DNA techniques as a way of improving plant varieties. The lack of a cell wall barrier offers significant advantages for the introduction of genetically engineered DNA.

Most of the predicted advantages of using plant cell protoplasts in agricultural improvements have not been realized in practice because of the difficulty in culturing and/or regenerating the cultured cells into intact plants. With the technique currently available it has been possible to achieve regeneration of protoplasts into whole plants in only a very limited number of instances and with marginal efficiencies. Regeneration from fused protoplasts extracted from plant leaves and stems has proven to be a viable method for the production of hybrids in a few instances, e.g. tobacco plant protoplasts have responded to known regeneration techniques and a number of hybrids have been thus produced. U.S. Pat. No. 3,832,801 shows a process for the regeneration of hybrids of the parent species *Nicotiana glauca* and *N. langsdorffi.*

Most of the important crop plants are refractory to currently available regeneration technology. For example, with respect to tomato plants, no process has been found for the regeneration of a viable plant from protoplasts.

The tomato (*Lycopersicon esculentum*) is an important crop plant and has proven to be one of the most versatile of cultivated plants. The agronomic value of the tomato was improved through the transfer of disease-resistance characteristics from other Lycopersicon species. Sexual hybrids between *L. esculentum* and the more closely related species are easily obtained. However, interspecific incompatibilities with some species limits the value of sexual hybridization for the introduction of important traits from wild species. Cell fusion and genetic engineering methods have been proposed to facilitate gene transfer in the tomato, but these methods require efficient plant regeneration from cultured protoplasts.

F. J. Zapata, P. K. Evans, J. B. Power and E. C. Cocking, "The effect of temperature on the division of leaf protoplasts of *Lycopersicon esculentum* and *Lycopersicon peruvianum*," *Plant Sci. Lett.* 8:119-124 (1977) disclose research with regard to the effect of temperature on the initiation and maintenance of cell division and callus formation with regard to mesophyll protoplasts of two tomato species, and note that while cell wall regeneration has been performed with isolated protoplasts, no sustained cell division has been reported when these protoplasts were cultured.

W. K. Coleman and R. I. Greyson, "Promotion of root initiation by giberrellic acid in leaf discs of tomato *Lycopersicon esculentum* cultured in vitro," *New Phytol.* 78:47-54 (1977) detail the use of gibberellic acid as a growth-promoting hormone.

A. C. Cassells and M. Barlass, "A Method for the isolation of stable mesophyll protoplasts from tomato leaves throughout the year under standard conditions," *Physiol. Plant.* 42:236-242 (1978) postulate that the failure of existing methods to regenerate plants from tomato mesophyll protoplasts is due to deficiencies in the culture medium, and suggest growing the protoplast-donating plants under specified conditions of nutrition and lighting.

E. Pojnar, J. H. M. Willison and E. C. Cocking, "Cell-wall regeneration by isolated tomato-fruit protoplasts," *Protoplasma* 64:460-480 (1969) have determined that cell wall regeneration may be helpful in the survival of isolated tomato protoplasts and disclose a method for such cell wall regeneration.

It is noted that none of these references detail a successful method for the regeneration of a cultivated tomato plant from protoplasts, and rather describe the extensive research in the art which has been directed to attaining such a result.

V. Padmanabhan, E. F. Paddock and W. R. Sharp, in "Plantlet formation from *Lycopersicon esculentum* leaf callus," *Can. J. Bot.* 52:1429-1432 (1974) describe the micropropagation of plants from cultivated tomato leaf callus, i.e. from callused leaf sections wherein the protoplasts are retained within their cell walls. This technique produces clones of a plant for varying purposes but does not enable the production of hybrids or allow genetic modification of the plants due to the fact that the protoplasts within the leaf sections are not freed for such manipulation.

Additional publications suggest the usefulness of a method for the production, from isolated protoplasts, of mature plants which have heretofore been incapable of such regeneration. For example, M. L. Kalil and A. C. Hildebrandt, "Effects of Agrobacterium sp. on cell cultures of tomato," *Phyton* 28:177-186 (1971) describe the isolation of protoplasts and the use of cell culturing methods to access aspects of the tumorization process. B. E. Ellis, "Non-differential sensitivity to the herbicide metribuzin in tomato cell suspension cultures," *Can. J. Plant Sci.* 58:775-778 (1978) describes the isolation of protoplasts and the use of cell suspension cultures to test the differential tolerance of tomato plants to the herbicide metribuzin.

C. P. Meredith, in "Response of cultured tomato cells to aluminum," *Plant Sci. Lett.* 12:17-24 (1978) describes the isolation of tomato protoplasts to determine significant differences in aluminum tolerance in cultivated plants. This reference discloses the measuring of such response by weighing individual callus pieces before and after exposure to aluminum in the culture medium. In a similar manner, C. P. Meredith, "Selection and characterization of aluminum-resistant variants from tomato cultures," *Plant Sci. Lett.* 12:25-34 (1978) describes the selection of callused cultured resistant cells, again tested by weight gain of the callus in a cultured medium. It is noted, at page 26, that the variant cells cannot be induced to regenerate plants.

A. C. Cassells, "Uptake of charged lipid vesicles by isolated tomato protoplasts," *Nature* 275:760 (1978) describes a method for the insertion of DNA into protoplasts which would be useful if plants could be regenerated therefrom.

While methods for the extraction of protoplasts which are capable of cell fusion or genetic manipulation are known, and workers have heretofore been successful in promoting the division of such cells, I am unaware of any process which enables the formation of viable, callused cell colonies, i.e. colonies which will eventually form mini-calli and shoots, from the isolated protoplasts of plants such as the cultivated tomato, cotton, members of the cucurbitaceae family, the brassica species, the euphorbia species, legumes such as soybeans and other plants which have hetertofore resisted such regeneration. This has appeared to be a critical step in the regeneration of tomato plants, as the mini-calli turn brown and die even in the most successful of the prior attempts at regeneration. As used herein, the term "mini-calli" refers to the callus which is formed on plant cell colonies, the mini-calli being barely visible, i.e. about two to three millimeters in diameter.

Thus, it has been a desideratum in the plant sciences to provide a reliable procedure for the production of viable callused cell colonies and for plant regeneration from protoplasts in plant species such as the cultivated tomato which have heretofore failed to respond to plant regeneration techniques.

In accordance with the present invention, a process is provided for plant regeneration from the protoplasts of plants which have heretofore resisted such techniques, and is described in some detail with regard to plant regeneration from protoplasts of the cultivated tomato.

While I do not wish to be bound by any particular theory, it is thought that certain plants which fail to regenerate from protoplasts do so due to the plant cell's inability to survive the cell extraction and culturing procedures. Specifically, cells which have developed in a natural state fail to grow in vitro because their natural hormone levels are incompatible with those of the artificial media. The natural hormones have been evolved by nature to produce a plant, not a protoplast which is viable in vitro. Consequently, the protoplasts fail to form viable calli, which then develop to form shoots, roots and plants. Thus, a method is provided whereby the source of the protoplast to be regenerated, i.e. the proto plast-donating plant, is a plant which has been preconditioned and treated, from its seed form throughout its life until the harvesting of the protoplasts, to prepare the cells for the regeneration regimen.

A seed consists of a dormant embryo, together with a quantity of stored nutrients and hormones, and one or two integuments which differentiate into the protective seed coat. The embryo may be an undifferentiated mass of cells, e.g. in the orchid family, but is usually more highly organized and consists of a short axis which is called the hypocotyl, which at one end bears a primitive root called the radicle and at the other end a terminal bud or plumule. Borne laterally at the apex of the hypocotyl just below the plumule are one or more seed leaves or cotyledons, which are filled with stored food material and form the greater part of the seed. The hormones which regulate the development of the embryo, the germination of the seed and the growth of the plant originate from within the embryonic tissue and are thus regarded as endogenous in origin. The major portion of these endogenous hormones is produced by the radicle.

Germination is the development of the embryo into a young plant. It becomes completed when the young plant is independent of the food and hormones stored in the seed. In most seeds, the first visible sign of germination is a swelling of the seed, which is a result of an increased water content. Often the seed coats are ruptured by the swelling of the contents of the seed. Respiration increases greatly, and much energy is made available to those regions where active growth occurs, that is, the hypocotyl and the plumule, which often push out of the seed to form a shoot. Finally, the radicle pushes out of the seed and attaches itself, by means of root hairs, to the soil particles. The roots then begin absorbing water and nutrients from the soil. Eventually, the plumule elongates and the first true leaves of the plant appear. With their formation, the plant becomes independent of the seed.

According to the invention, the protoplast is isolated from a protoplast-donating organism which has been grown in the substantial absence of endogenous hormones, as opposed to isolating the protoplast from a natural plant. The growth of the donating organism in the substantial absence of endogenous material is thought to precondition the organism so that the protoplasts are prepared for the in vitro environment and artificial hormone levels required by the regeneration procedure. For example, the protoplast-donating plants may be preconditioned by being grown from seed-generated shoots which have had the radicle neutralized or removed so that the nutrients and hormones contained in those portions do not substantially contribute to the growth of the shoot.

In another aspect of the invention, the protoplasts are cultured in a defined media sequence having a controlled regimen with regard to osmoticum, ammonia-producing salts and hormones to support and regulate the further growth of the protoplast and the formation of colonies, calli, roots and young plants.

Other varied preconditioning steps may be desirable for the protoplast regeneration of a particular plant. For example, it may be particularly helpful to grow the protoplast-donating plants in an artificial medium which is substantially free of all growth regulating hormones in order to enhance the extraction of viable protoplasts therefrom. Maintaining the donating plants in the absence of light for a period prior to the protoplast extraction has been shown to aid in the extraction of the protoplasts therefrom. However, it is thought essential to the practice of the invention that the protoplast-donating organism be deprived of a substantial portion of its normal endogenous growth regulators to ensure the survival and viable growth of the isolated protoplasts.

With regard to the growth media of the present invention, the terms "growth medium" or "nutrient medium" as used herein comprise a solution of the mineral salts and vitamins necessary for plant growth, generally containing combined nitrogen, potassium, phosphorous, calcium, sulphur and magnesium with traces of iron, boron, zinc, copper and various organic substances. Thus, the growth media employed in the various steps of the regeneration process may be any medium understood by those skilled in the art to provide the nutrients necessary for plant cell growth. However, it should be noted that improvements in the survival and growth of the protoplasts result from providing for a substantial similarity among the nutrient media and solutions employed in the described process so that the transport shock to the protoplasts, cell colonies, calli, shoots and roots is reduced. As used herein, the term "substantially similar" is intended to mean that aside from constituents which must be increased or decreased at a particular point in order to have a specific effect on growth or survival, such as sugars, ammonium salts, buffers and various hormones or vitamins, the components of the medium or solution do not essentially vary beyond the limits expressed herein.

Specifically, with regard to the media that support the isolated protoplasts and colonies formed therefrom, i.e. the free cell media, it is essential that the osmoticum (a measure of the osmotic pressure of the fluid quantified as the molarity of the sugars therein) should be increased to provide support for the wall-less cells, and the ammonium and nitrogen-containing salts which produce ammonia must be reduced or substantially eliminated. In the free cell media as well as in other media and solutions, specific hormones are included to promote the particular effect. Specific examples of the effect of various hormones and ammonium ions on callus formation are set forth in "Callus Formation from Leaf Mesophyll Protoplasts of Three Lycopersicon Species", Zapata et al., Plant Science Letters, 23 (1981) 41–46, which is hereby incorporated by reference.

While the invention is hereinafter described with regard to tomato cultivar Red Cherry and VF-36 varieties, UC-82, Lorz Cherry, Floradade, Cocktail Cherry, Manapal and VFNT-Cherry varieties have also been regenerated from protoplasts according to the method of the invention. Other crop plants which have heretofore been difficult or impossible to regenerate from somatic cells such as cotton, legumes, e.g. soybeans, members of the cucurbitaceae family, the brassica species and the euphorbia species are also generated according to the process hereinafter set forth, and the method of the invention provides distinct advantages in the protoplast regeneration of all plants and improves regeneration processes heretofore known.

BRIEF DESCRIPTION OF THE DRAWINGS

FIG. 1 shows freshly isolated protoplasts ×1,200;

FIG. 2 shos cell division after four days of culture ×1,200;

FIG. 3 shows a cell colony after six days of culture ×1,200;

FIG. 4 is a callus formed after twelve days of culture;

FIG. 5 shows shoot regeneration after twenty-one days of culture;

FIG. 6 shows the mature plant; and

FIG. 7 is a schematic sequence of the regeneration process.

DETAILED DESCRIPTION OF THE PREFERRED EMBODIMENT

Figure 1:
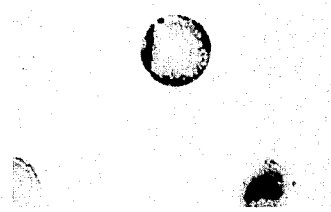
FIGS. 1–6 are reproductions of photographs which show the various stages in the isolation and development of a Red Cherry protoplast and the regeneration of a mature plant therefrom.
Figure 2:
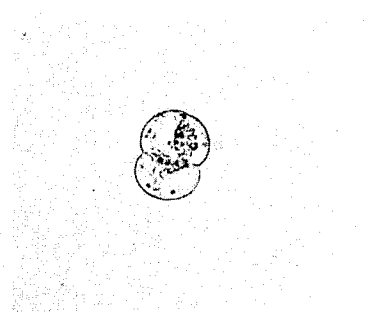
Figure 3:
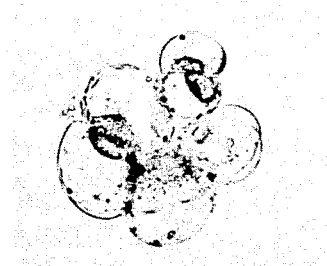
Figure 4:
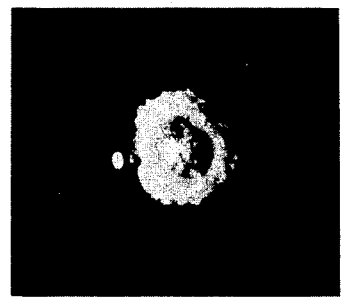
Figure 5:
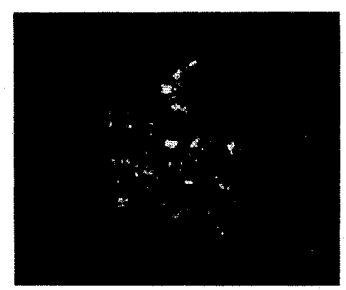
Figure 6:
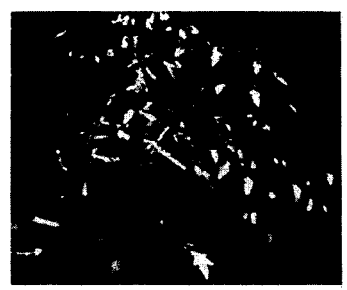

With regard to the embodiment hereinafter set forth, which relates to the regeneration of cultivated tomato plants, the preconditioning first includes the germination of a seed from a tomato plant until the cotyledons and a substantial portion of the hypocotyl extend from the opened seed, i.e. until a shoot is formed. This extending shoot portion, that is, the cotyledons and the section of the hypocotyl proximal thereto, is then removed from the radicle or root section of the hypocotyl to substantially isolate the shoot portion from the endogenous hormones and nutrients which are contained therein. The shoot portion is then grown in a medium which is substantially free of growth hormones, as hereinafter described, to form the protoplast-donating plant.

The preferred nutrient media employed in the growth of the protoplast-donating plant and the regeneration of the mature plant from the protoplast are described in Table 1, wherein TM-1 is the medium for growing the protoplast-donating plants; TM-2 is the plating medium; TM-3 is the callus-forming medium; TM-4 is the shoot-forming medium; and TM-5 is the root-forming medium. Among the major salts, the ammonium salts are notably absent from the TM-2 and TM-3 media to remove the source of free ammonia which would otherwise substantially reduce the pH of the media and have a toxic effect on the free cells therein. The potassium nitrate has been reduced in the free cell media to lower the nitrogen content which is thought to have the same effect. While the other major salts vary slightly or are omitted where unnecessary, such variations and omissions are preferred only and may be included in any amount which is known in the art.

The minor salts are seen to be included in constant amounts to perform known metabolic functions. The vitamins are also seen to be included in constant amounts in the five media, except for nicotinic acid which is provided in reduced amounts in TM-1 and TM-2 as it could possibly have toxic effects therein; D-Ca-pantothenate, choline chloride, ascorbic acid and riboflavin which are omitted from TM-3, -4 and -5 due to the fact that the cells begin to produce these substances themselves after colony formation; L-cysteine and malic acid, which are useful only at the early stages of cell growth; and casein hydrolysate and myo-inositol which are beneficial in increased amounts in the TM-2 medium. However, the variations in the amount of vitamins in the five media are not critical, and all could be maintained at the TM-1 level without substantially affecting the regeneration process.

Adenine sulfate and L-glutamine, which promote cell growth, are included in the free cell media but omitted from TM-1, TM-4 and TM-5 since they are not critical therein. MES buffer is included in the TM-2 medium to enhance cell division and growth, and to maintain the pH of the plating solution. This is due to the fact that actively growing cells release substances which lower the pH of a medium with a resultant toxic effect on the cells.

The osmotic effect of the media, or osmoticum, is seen to be provided by sucrose and the sugar-alcohols mannitol, xylitol and sorbitol. The sugar alcohols are included in the TM-2 medium as they are thought to enhance cell growth. While the osmotic effect of a medium may vary depending upon the species of the protoplast being cultured or regenerated, it is critical that the free cell media have an osmotic effect which is high enough to support the wall-less cells in a spherical form and prevent an unbalanced osmotic pressure with respect to the cell contents. With regard to the TM-2 medium which supports the cells before substantial walls are formed, an osmoticum of about 0.2M to about 0.35M is required. In the TM-3 medium, which supports the cell colonies during callus formation, an intermediate osmoticum is provided having a minimum of about 0.12M. The osmoticum of the remaining nutrient media, which need not support free cells, is provided at 0.09M.

The various hormones employed in the regeneration process are set forth, along with the abbreviations therefor, in Table 9. As used herein, "hormone" refers to an organic compound, either natural or synthetic, that modifies or controls one or more specific physiological or biochemical processes within the plant.

In general, the auxins are understood to be natural or synthetic plant growth hormones that regulate plant cell enlargement and the cytokinins promote cell division and differentiation. In addition to the hormones listed in Table 9, other analogs of the described hormones or derivatives such as BAP riboside or kinetin riboside may be used to produce the desired morphogenic response in the particular medium.

In this regard, TM-1 is seen to be free of hormones so that the cells of the protoplast-donating organism, rather than being directed toward the formation of a mature plant, are maintained in an isolated environment to preclude the transport shock of isolation, i.e. the cells are preconditioned for the in vitro procedures hereinafter described.

The TM-2 medium is seen to include cell growth and a division-regulating hormone moiety. As described, the auxin component (NAA) promotes cell growth and DNA synthesis, and the cytokinin (Zn-R) promotes cell division. With regard to the ZN-R, other cytokinins, such as BAP, kinetin or 2iP may be substituted for Zn-R, and similarly other auxins may be substituted for NAA as is known in the art.

With regard to TM-3, a callus-forming hormone moiety is provided as is hereinafter described. It should be noted that an excess of auxin in the callus-forming medium tends to carry over and increase the auxin-to-cytokinin ratio in the succeeding shoot-forming step, and thus has a deleterious effect on the shoot formation. In that regard, the shoot-forming hormones in TM-4 are seen to be provided in an auxin-to-cytokinin ratio of less than one (on a molar basis) to promote the formation of shoots.

The TM-5 medium is seen to include IBA, a root-forming hormone, although 3-amino pyridine, other auxins, commercial root inducing preparations, or root-forming combinations of auxins and cytokinins may be substituted. In this regard, combinations having an auxin-to-cytokinin ratio of greater than one (on a molar basis) are necessary to induce root formation.

Turning now to Table 2, the enzymatic protoplast extraction solutions will be described. The solutions described in Table 2 are seen to include the major salts set forth in Table 1, absent the ammonium salts for reasons hereinbefore described, and the vitamins in amounts shown for the TM-1 medium. The amounts of the major salts and the vitamins shown are not critical within limits recognized by those skilled in the art, and the addition of the minor salts in amounts shown in Table 1 have been shown not to substantially affect the survival of the extracted cells. The critical aspects of the solutions of Table 2 are both the osmoticum, which must be 0.15M or more to provide cell support in the free cell solutions, and the absence of toxic amounts of ammonium salts.

Preferably, the solutions contain sufficient sucrose to provide a 0.3M solution. The PET solution, wherein leaf fragments are suspended for one to two days before the extraction process, preferably contains auxin and cytokinin hormones to precondition the protoplasts, while still in their natural state, for their first exposure to hormones in the TM-2 medium. This hormone preconditioning has been found to produce optimal results in the subsequent steps.

The enzyme solution is seen to include macerozyme and cellulysin enzymes which are preferred to release the protoplasts from the leaf fragments. Other extraction enzymes and procedures, known in the art, may be employed, such as the method set forth by De Wit in "Isolation and Culture of Tomato Mesophyll Protoplasts", *Acta Bot. Neerl.* 25(6), p. 475–80 (December 1976), which is hereby incorporated by reference.

The rinse solution preferably contains a buffer similar to that employed in the subsequent TM-2 medium.

Due to the nature of the growth medium which, of course, facilitates the growth of most organisms, it is necessary to maintain the seeds, growth medium, plant containers, plantlets and support media in a sterile condition to avoid the growth of ambient bacteria and fungi which would otherwise overwhelm the plants.

Additional preconditioning steps are also beneficial to the growth of the plantlets and the survival of the protoplasts cultured therefrom. For example, the plants may be kept in a growth chamber under alternating light and dark conditions, i.e. sixteen hours light followed by eight hours dark. After the plantlets are grown and before the protoplasts are enzymatically removed therefrom, the plantlets may be placed in substantial darkness for the forty-eight hours immediately preceding the enzyme treatment.

The protoplasts which are isolated from the donating plantlet are then plated in a nutrient medium which is substantially similar to the medium which provided nutrients to the plantlet. Thereafter, the protoplasts are cultured to form multi-cellular colonies in a medium which is, again, substantially similar to the previously used media except that cell-growth hormones are included therein. The multi-cellular colonies are then grown in a similar medium containing callus-forming hormones to generate a callus on each colony. The callused colonies are then grown in the presence of appropriate hormones until shoots are formed thereon. Thereafter, the shoots are grown in a similar medium containing a root-forming hormone until roots are developed, and when the rooted plantlets are sufficiently developed they are transferred to soil for further growth.

EXAMPLE ONE

Tomato cultivar Red Cherry seedlings were surface-sterilized by immersion for twenty minutes in a solution of 1.08% sodium hypochlorite. After being rinsed thoroughly with sterile, distilled water, the seeds were germinated on a presterilized filter paper in glass petri dishes. Three days after germination, when the cotyledons and a substantial section of the hypocotyl extended from the seeds to form a shoot, the radicle and seed were dissected from the shoot, and the shoots were transferred to a "Plant-Con" closed, transparent growth vessel containing 100 ml of TM-1 medium. The TM-1 medium and other media hereinafter discussed are shown in Table 1. The sprouts were kept in the growth chamber at 26° C., sixteen hours light, eight hours dark at 4,800 lux light intensity until plantlets of approximately 12 cms high were formed. Thereafter, the plantlets were removed from the vessel and placed in a dark chamber at 26° C. for two days.

After the dark treatment, the leaf tissue was cut into small fragments (0.5 cm) and 0.67 grams of leaf tissue was soaked in 50 ml of PET solution in a 250 ml flask for sixteen hours at 10° C. The composition of the PET solution and the enzyme solution hereinafter discussed are set forth in Table 2.

The next day, the PET solution was decanted, and replaced by an enzyme solution to isolate the protoplasts from the leaf fragments. 30 ml of the enzyme solution was added to 1 gram of leaf material, and the enzyme solution was then infiltrated into the leaf tissue by a vacuum. The flask containing the enzyme solution was placed in a water bath shaker rotating at 60 rpm and maintained at a temperature of 28° C. for seven hours. At the end of this time, the protoplasts were harvested by centrifugation at 50 xg for ten minutes using Babcock bottles. The protoplasts were floated to the top and then collected with a sterile Pasteur pipet. The protoplasts were washed once with a rinse solution (Table 2), and resuspended in a holding solution (TM-2 without hormones) for sixty minutes and counted with a hemacytometer. The yield was $1.8 \times 10^6$ protoplasts/g leaf tissue.

The protoplasts were plated in TM-2 medium at a density of 30,000/ml media in 2 ml aliquot/petri dishes (60×15 mm). The petri dishes were sealed with parafilm, and then incubated at 25° C. in diffused light (500 lux) at sixteen hours light/eight hours dark photoperiod.

Five days later, the plates were examined and cell division was noticed (5–6 cells) among the newly-formed cells. The controls contained a medium with a higher osmoticum (0.5M instead of 0.2M) and in this medium no cell wall formation or division occurred.

After four more days, the colonies were transferred to the TM-3 medium, which has a lower osmoticum to encourage rapid growth. By using pasteur pipets with a wide tip, 1 ml of the suspension was picked up and dispersed on to the surface of the TM-3 medium. Only the contents of one plate of each of the TM-2 media was transferred to TM-3. The rest were kept intact for three more days. It was later found that the cell colonies of this particular species must be transferred to the lower osmoticum medium within ten days after plating, or else they will develop a brown callus and fail to further develop due to the inhibitory byproducts accumulated in the TM-2 medium.

The colonies were then kept in the TM-3 medium under diffuse light (500 lux) of sixteen hours per day for one week. The plating efficiency (P.E.) of the protoplasts was calculated on the twelfth day after plating prior to transferring the mini-calli into shooting media TM-4 according to the formula:

$$P.E. = \frac{\text{number of mini-calli} \times 100\%}{\text{Total number of protoplasts}}$$

Calli were developed more readily on colonies cultured in TM-3 medium supplemented with 2,4-D and BAP than NAA and BAP as is shown in Table 3. Although some calli were developed in the TM-3 media supplemented with NAA and BAP, when these mini-calli were placed into various shooting media, there was no morphogenic response. On the other hand, when calli developed on TM-3 medium supplemented with 2,4-D and BAP were placed on various shooting media, shoot regeneration occurred in all cases. These experiments, and others, indicate that derivatives of phenoxyacetic acids, i.e. 2,4-D; 2,4S-T and PCT are particularly advantageous in the callus forming medium.

It should be noted that the hormones employed in an early stage may carry over and affecta succeeding state. For example, a higher concentration of auxin in the TM-3 medium may not inhibit callus formation, yet may be transported within the callused cell colonies to the shooting medium where it will inhibit shoot formation.

After six days in the TM-3 medium, the protoplast-derived mini-calli were transferred to TM-4 medium. Ten calli were placed on each plate and cultured under an illumination of 4,800 lux for sixteen hours per day photoperiod at 25° C. and shoots were formed after twelve days. Regenerated shoots were then dissected from the callus and cultured on TM-5 medium which contains IBA, a root-forming hormone of the auxin class. Two to three weeks after root formation, the rooted plantlets were well developed and were transferred to four-inch pots containing a soil-vermiculite mixture after removing the agar, and placed in a growth chamber at 25° C. constant temperature, with a sixteen hour photoperiod at a light intensity of 6,000 to 7,000 lux. Plants were watered once a day and fertilized with 20:20:20 fertilizer (1 gram per liter) once a week.

EXAMPLE TWO

Tomato cultivar VF-36 seeds were surface-sterilized by immersion in sodium hypochlorite, and after being rinsed thoroughly with sterile, distilled water, were germinated on presterilized filter paper in glass petri dishes. Three days after germination, the excised shoots were grown in the agar of TM-1 medium for about three weeks under aseptic conditions at a temperature of 25° C. for a sixteen hour photoperiod at 4,800 lux light intensity. The plants were then removed from the incubator and placed in a dark chamber at 25° C. for two days. Thereafter, the leaves were cut into small pieces and placed into PET solution for fifteen hours at 10° C. The net weight of the leaf tissue was 0.75 grams. Similarly, the stems were cut into small pieces and placed in PET solution under the same conditions.

After fifteen hours, the PET solution was decanted and replaced by the enzyme solution detailed in Table 2. The flask containing the enzyme solution was placed on a shaker bath at 28° C. and 60 rpm for a period of ten hours. Thereafter, the protoplasts were collected by centrifugation in Babcock bottles and $4.0 \times 10^6$ protoplasts per gram of leaf material and $3.33 \times 10^6$ protoplasts per gram of stem material were obtained.

The protoplasts were plated in TM-2 medium having various growth hormone combinations described in Table 5. Plating density was 10,000, 15,000 and 20,000 protoplasts per milliliter medium in a 6×15 mm petri dish.

Table 5 illustrates the results of protoplast reaction to the plating medium in the presence of various combinations of growth hormones under various plating densities. Both stem and leaf protoplasts divided and formed calli abundantly when plated at 20,000 per milliliter. It is noteworthy to mention that plant protoplast division requires certain minimum plating density, which may be determined without undue experimentation for each plant specie under the proposed culture conditions.

Soon after the formation of cell colonies, twelve days after plating, the colonies were transferred onto the surface of TM-3 agar medium for mini-callus formation. 0.1 ml aliquots from the cell colony suspension were diluted with 0.4 ml solution of TM-2 medium minus the hormones. This dilution was then applied to the surface of the TM-3 agar and allowed to settle. This procedure allowed dilution of cell colonies so that they could be counted thereafter. Five days later, the mini-calli were obvious on the agar surface and were counted. The plating efficiency was determined as 20.15 and 21.62%.

Experiments with regard to the advantages of phenoxyacetic acid derivatives as callus forming hormones showed results identical to those expressed in Table 3.

The mini-calli were then transferred individually onto the agar surface of various shooting media based on the TM-4 medium in combination with various growth regulators. The plates were incubated at 25° C. under 4,800 lux light intensity and a sixteen-hour photoperiod. The results are shown in Table 6. It appears that the VF-36 calli regenerated into shoots similar to those described in Example One, but the frequency of regeneration was much lower, i.e. 24-33%. It was identified that the regeneration of the VF-36 calli was lower due to the fact that while preparing the media, trans-isomer zeatin form was used instead of the crystalline zeatin riboside form which was used with the Red Cherry tomatoes. To support this observation, both zeatin and zeatin riboside were used separately in TM-4 medium for shoot regeneration. Table 7 shows the results of this undertaking. When trans-isomer zeatin was used in the TM-4 medium instead of zeatin riboside, the frequency of regeneration dropped at least 60%. Furthermore, this reaction occurred in both stem and leaf protoplast-derived calli. In a parallel experiment, kinetin, another active cytokinin, replaced zeatin riboside in TM-4 media. These results are summarized in Table 8.

Shoots that were 1 to 2 cm long were detached from their calli and placed onto agar of the TM-5 medium. The shoots were then incubated at 20° C., with a sixteen-hour photoperiod of 4,800 lux light intensity. Root formation occurred two weeks later and the young plants were ready for planting in the soil. Small shoots, however, less than 1 cm long, were subcultured onto TM-4 medium with a small amount of callus material attached to them. Ten days later, the shoots had elongated and were ready to go onto rooting medium (TM-5). Of a total of 127 small shoots, 120 shoots were ready by the tenth day due to that process. Having been placed in the rooting medium, the plants attained an average height of 10 cm within fifteen days.

Although the foregoing invention has been described in some detail by way of illustration and example, changes in form and the substitution of equivalents are contemplated as circumstances may suggest or render expedient; and although specific terms have been employed herein, they are intended in a descriptive sense and not for purposes of limitation, the scope of the invention being delineated in the claims.

TABLE 1

Constituents and concentrations of tomato culture media.

| | mg/l | | | | |
|---|---|---|---|---|---|
| | TM-1 | TM-2 | TM-3 | TM-4 | TM-5 |
| MAJOR SALTS | | | | | |
| $KH_2PO_4$ | — | 170 | 170 | — | — |
| $CaCl_2 2H_2O$ | 150 | 440 | 440 | 150 | 75 |
| $KNO_3$ | 2,530 | 1,500 | 1,500 | 1,900 | 1,265 |
| $NH_4NO_3$ | 320 | — | — | 320 | 160 |
| $NH_4H_2PO_4$ | 230 | — | — | 230 | 115 |
| $(NH_4)_2SO_4$ | 134 | — | — | 134 | 67 |
| $MgSO_4 7H_2O$ | 250 | 370 | 370 | 247 | 125 |
| MINOR SALTS | | | | | |
| KI | 0.83 | 0.83 | 0.83 | 0.83 | 0.83 |
| $H_3BO_3$ | 6.20 | 6.20 | 6.20 | 6.20 | 6.20 |
| $MnSO_4 4H_2O$ | 22.30 | 22.30 | 22.30 | 22.30 | 22.30 |
| $ZnSO_4 7H_2O$ | 8.60 | 8.60 | 8.60 | 8.60 | 8.60 |
| $Na_2MoO_4 2H_2O$ | 0.25 | 0.25 | 0.25 | 0.25 | 0.25 |
| $CuSO_4 5H_2O$ | 0.025 | 0.025 | 0.025 | 0.025 | 0.025 |
| $CoCl_2 6H_2O$ | 0.025 | 0.025 | 0.025 | 0.025 | 0.025 |
| $FeSO_4 7H_2O$ | 13.90 | 13.90 | 13.90 | 13.90 | 13.90 |
| $Na_2EDTA$ | 18.50 | 18.50 | 18.50 | 18.50 | 18.50 |
| VITAMINS | | | | | |
| Nicotinic acid | 2.50 | 2.50 | 5.0 | 5.0 | 5.0 |
| Thiamine HCl | 10.00 | 10.00 | 0.5 | 0.5 | 0.5 |
| Pyridoxine HCl | 1.00 | 1.0 | 0.5 | 0.5 | 0.5 |
| Folic acid | 0.50 | 0.50 | 0.50 | 0.50 | 0.50 |
| Biotin | 0.05 | 0.05 | 0.05 | 0.05 | 0.05 |
| D-Ca—Pantothenate | 0.50 | 0.50 | — | — | — |
| Choline Chloride | 0.10 | 0.10 | — | — | — |
| Ascorbic Acid | 0.50 | 0.50 | — | — | — |
| Glycine | 0.50 | 0.50 | 2.50 | 2.50 | 2.50 |
| Casein hydrolysate | 50.00 | 150 | 100 | 100 | 100 |
| L-Cysteine | 1.00 | 1.00 | — | — | — |
| Malic Acid | 10.00 | 10.00 | — | — | — |

TABLE 1-continued

Constituents and concentrations of tomato culture media.

| | TM-1 | TM-2 | TM-3 | TM-4 | TM-5 |
|---|---|---|---|---|---|
| | | | mg/l | | |
| Myo-inositol | 100.00 | 4660.00 | 100.00 | 100.00 | 100 |
| Riboflavin | 0.25 | 0.25 | — | — | — |
| OTHER | | | | | |
| Adenine Sulfate | — | 40.00 | 40.0 | — | — |
| L-Glutamine | — | 100.00 | 100.00 | — | — |
| MES buffer | — | 97.60 | — | — | — |
| OSMOTICUM | 0.09 M | 0.275 M | 0.15 M | 0.09 M | 0.09 M |
| Sucrose | 30,000 | 68,400 | 50,000 | 30,000 | 30,000 |
| Mannitol | — | 4,560 | — | — | — |
| Xylitol | — | 3,800 | — | — | — |
| Sorbitol | — | 4,560 | — | — | — |
| HORMONES | | | | | |
| NAA | — | 1.0 | — | — | — |
| Zeatin Riboside | — | 0.5 | — | 1.0 | — |
| 2,4-D | — | — | 0.2 | — | — |
| BAP | — | — | 0.50 | — | — |
| GA$_3$ | — | — | — | 0.2 | — |
| IBA | — | — | — | — | 0.1 |
| Agar | 6,000 | — | 7,000 | 7,000 | 9,000 |
| pH | 5.8 | 5.6 | 5.8 | 5.8 | 5.8 |

TABLE 2

| | PET | Enzyme Solution | Rinse Solution |
|---|---|---|---|
| | Mg/l except as noted | | |
| Major salts | | | |
| KH$_2$PO$_4$ | 42.50 | 85.00 | 85.00 |
| CaCl$_2$2H$_2$O | 110.00 | 220.00 | 220.00 |
| KNO$_3$ | 375.00 | 750.00 | 750.00 |
| MgSO$_4$7H$_2$O | 92.50 | 185.00 | 185.00 |
| Vitamins | | | |
| Nicotinic Acid | 2.50 | 2.50 | 2.50 |
| Thiamine HCl | 10.00 | 10.00 | 10.00 |
| Pyridoxine HCl | 1.00 | 1.00 | 1.00 |
| Folic Acid | 0.50 | 0.50 | 0.50 |
| Biotin | 0.05 | 0.05 | 0.05 |
| D Ca Pantothenate | 0.50 | 0.50 | 0.50 |
| Choline Chloride | 0.10 | 0.10 | 0.10 |
| Ascorbic Acid | 0.50 | 0.50 | 0.50 |
| Myo-inositol | 100.00 | 100.00 | 100.00 |
| Glycine | 0.50 | 0.50 | 0.50 |
| L-Cysteine | 1.00 | 1.00 | 1.00 |
| Caesin hydrolysate | 50.00 | 50.00 | 50.00 |
| Malic Acid | 10.00 | 10.00 | 10.00 |
| Riboflavin | 0.25 | 0.25 | 0.25 |
| Osmoticum | 0.30 M | 0.30 M | 0.30 M |
| Sucrose | 102.60 g/l | 102.60 g/l | 102.60 g/l |
| Hormones | | | |
| 2,4-D | 1.0 | | |
| BAP | 0.5 | | |
| Others | | | |
| MES Buffer (2-N—Morpholino-ethane Sulfonic acid) | — | 1.00% (w/v) | 97.60 |
| PVP-10 | | | |
| Enzymes | | | |
| Macerozyme | — | 0.10% (w/v) | — |
| Cellulysin | — | 0.75% (w/v) | — |
| pH | 5.8 | 5.6 | 5.8 |

TABLE 3

Callus formation from mesophyll protoplasts of the Red Cherry tomato in response to various hormone combination and concentration.

| TM-2 Basal Medium Hormone (mg/l) | | | | | TM-3 Basal Medium Hormone (mg/l) | | | Callus Formation |
|---|---|---|---|---|---|---|---|---|
| 2,4-D | NAA | BAP | ZN | KIN | NAA | 2,4-D | BAP | |
| 1.0 | — | .5 | — | — | — | .5 | .25 | + |
| 1.0 | — | .5 | — | — | 1.0 | — | .5 | + |
| 0.5 | 0.2 | 0.2 | 0.2 | 0.2 | 1.0 | — | .5 | — |
| 0.5 | 0.2 | 0.2 | 0.2 | 0.2 | — | .5 | .25 | + |
| 1.0 | — | — | — | 0.5 | — | .5 | .25 | + |
| 1.0 | — | — | — | 0.5 | 1.0 | — | .5 | — |
| 0.5 | — | — | 0.2 | — | 1.0 | — | .5 | — |
| 0.5 | — | — | 0.2 | — | — | .5 | .25 | + |
| 0.5 | 1.0 | — | — | 1.0 | — | .5 | .25 | + |
| 0.5 | 1.0 | — | — | 1.0 | 1.0 | — | .50 | — |

TABLE 4

Formation of shoots by calli derived protoplasts as influenced by sequence and concentration of hormones in TM-3 media.

| Plating Medium | Callus Medium | Shooting Medium | Morphogenic Response |
|---|---|---|---|
| TM-2(2,4-D/BAP) | TM-3(NAA/BAP) | TM-4(2 μM Kinetin) | — |
| TM-2(2,4-D/BAP) | TM-3(NAA/BAP) | TM-4(5 μM Kinetin) | — |
| TM-2(2,4-D/BAP) | TM-3(NAA/BAP) | TM-4(1 μM IAA, 20 μM 2iP) | — |
| TM-2(2,4-D/BAP) | TM-3(NAA/BAP) | TM-4(4.56 μM Zn) | — |
| TM-2(2,4-D/BAP) | TM-3(NAA/BAP) | TM-4(11.5 μM Kn, 45 μM IAA) | — |
| TM-2(2,4-D/BAP) | TM-3(NAA/BAP) | TM-4(1 μM GA$_3$, 5 μM Kn, 3 μM IAA) | — |
| TM-2(2,4-D/BAP) | TM-3(NAA/BAP) | TM-4(1 μM GA$_3$, 10 μM Kn, 3 μM IAA) | — |
| TM-2(2,4-D/BAP) | TM-3(NAA/BAP) | TM-4(1 μM GA$_3$, 5 μM Kn) | — |
| TM-2(2,4-D/BAP) | TM-3(NAA/BAP) | TM-4(5 μM BAP, 1 μM GA$_3$, 1 μM IAA) | — |
| TM-2(2,4-D/BAP) | TM-3(NAA/BAP) | TM-4(2 μM GA$_3$, 7 μM Kn, 3 μM IAA) | — |
| TM-2(2,4-D/BAP) | TM-3(NAA/BAP) | TM-4(1 μM GA$_3$, 5 μM Zn—R) | — |
| TM-2(2,4-D/BAP) | TM-3(2,4-D/BAP) | TM-4(2 μM Kinetin) | + |
| TM-2(2,4-D/BAP) | TM-3(2,4-D/BAP) | TM-4(5 μM Kinetin) | + |

TABLE 4-continued

Formation of shoots by calli derived protoplasts as influenced by sequence and concentration of hormones in TM-3 media.

| Plating Medium | Callus Medium | Shooting Medium | Morphogenic Response |
|---|---|---|---|
| TM-2(2,4-D/BAP) | TM-3(2,4-D/BAP) | TM-4(1 μM IAA, 20 μM 2iP) | + |
| TM-2(2,4-D/BAP) | TM-3(2,4-D/BAP) | TM-4(4.56 μM Zn) | + |
| TM-2(2,4-D/BAP) | TM-3(2,4-D/BAP) | TM-4(11.5 μM Kn, 45 μM IAA) | + |
| TM-2(2,4-D/BAP) | TM-3(2,4-D/BAP) | TM-4(2 μM $GA_3$, 5 μM Kn, 3 μM IAA) | + |
| TM-2(2,4-D/BAP) | TM-3(2,4-D/BAP) | TM-4(1 μM $GA_3$, 10 μM Kn, 3 μM IAA) | + |
| TM-2(2,4-D/BAP) | TM-3(2,4-D/BAP) | TM-4(1 μM $GA_3$, 5 μM Kn) | + |
| TM-2(2,4-D/BAP) | TM-3(2,4-D/BAP) | TM-4(5 μM BAP, 1 μM $GA_3$, 3 μM IAA) | + |
| TM-2(2,4-D/BAP) | TM-3(2,4-D/BAP) | TM-4(2 μM $GA_3$, 7 μM Kn, 3 μM IAA) | + |
| TM-2(2,4-D/BAP) | TM-3(2,4-D/BAP) | TM-4(1 μM $GA_3$, 5 μM Zn—R) | + |

TABLE 5

Response of VF-36 protoplasts to various growth hormones in the plating medium (TM-2) under the influence of plating density

| BASAL MEDIUM (TM-2) Growth Hormones (mg/l) | | | | | | Plating | |
|---|---|---|---|---|---|---|---|
| NAA | BAP | Zeatin | 2,4-D | Kinetin | p-CPA | Density | Protoplasts response |
| 1.0 | — | 0.5 | — | — | — | 10K | no division, dead |
| — | — | 0.5 | — | — | 1.0 | 10K | no division, dead |
| — | 0.5 | — | 1.0 | — | — | 10K | few calli |
| — | 0.5 | — | — | — | 1.0 | 10K | few calli |
| 1.0 | — | — | 0.5 | 1.0 | — | 10K | few calli |
| 0.2 | 0.2 | 0.2 | 0.5 | 0.2 | 0.2 | 10K | abundant calli |
| 0.2 | 0.2 | 0.2 | 0.5 | 0.2 | 0.2 | 15K | abundant, large calli |
| 1.0 | — | 0.5 | — | — | — | 15K | no calli |
| — | — | 0.5 | — | — | 1.0 | 15K | no calli |
| 1.0 | — | 0.5 | — | — | — | 20K | abundant calli |
| — | — | 0.5 | — | — | 1.0 | 25K | abundant calli |
| — | — | 0.5 | — | — | 1.0 | 20K | abundant calli |

TABLE 6

Shoot initiation response of VF-36 tomato protoplast-derived callus on basal TM-4 medium supplemented with various combinations of growth hormones.

| TM-2 MEDIUM Growth hormones (mg/l) | | | SHOOTING MEDIUM (TM-4) Growth hormones (mg/l) | | | | | | Response |
|---|---|---|---|---|---|---|---|---|---|
| Code | CPA | NAA | ZN | Code | $GA_3$ | $ZN^1$ | KN | IAA | 2iP | Shoot/Callus (%) |
| C/Z | 1.0 | — | 0.5 | TSM-8I/K | — | — | 2.5 | 8.0 | — | 5/130 (3.85) |
| C/Z | 1.0 | — | 0.5 | TSM-4$G^2$ | 0.2 | 1.0 | — | — | — | 31/110 (28) |
| C/Z | 1.0 | — | 0.5 | TSM-4 | 0.2 | 1.0 | — | — | — | 35/110 (31.82) |
| $C/Z^3$ | 1.0 | — | 0.5 | TSM-4G | 0.2 | 1.0 | — | — | — | 6/70 (8.57) |
| $C/Z^3$ | 1.0 | — | 0.5 | TSM-4 | 0.2 | 1.0 | — | — | — | 6/70 (8.57) |
| $C/Z^3$ | 1.0 | — | 0.5 | TSM-12 | 0.2 | — | 1.0 | — | — | 1/10 (10) |
| $C/Z^3$ | 1.0 | — | 0.5 | TSM-8I/K | — | — | 2.5 | 8.0 | — | 0/60 Brown calli |
| N/Z | — | 1.0 | 0.5 | TSM-4 | 0.2 | 1.0 | — | — | — | 24/100 (24) |
| N/Z | — | 1.0 | 0.5 | TSM-8I/K | — | — | 2.5 | 8.0 | — | 1/30 (3.3) |
| N/Z | — | 1.0 | 0.5 | TSM-25 | 0.2 | — | — | — | 2.0 | 0/20 dead |
| N/Z | — | 1.0 | 0.5 | TSM-26 | 0.2 | — | — | — | 1.0 | 0/20 dead |

[1] Zeatin was used instead of zeatin riboside.
[2] Glucose (2.0%) was used instead of sucrose 3.0%.
[3] C/Z stem protoplasts.

TABLE 7

Percentage of VF-36 mini-calli developing shoots after 3 weeks of culture on TM-4 medium containing different form of zeatin.

| | TM-2 Medium Growth hormones (mg/l) | | | Shooting Medium (TM-4) Growth regulators (mg/l) | | | Response |
|---|---|---|---|---|---|---|---|
| | p-CPA | NAA | Zeatin | $GA_3$ | Zeatin | Zeatin Riboside | Shoots/callus (%) |
| Stem protoplasts | 1.0 | — | 0.5 | 0.2 | — | 1.0 | 53/70 (76) |
| | 1.0 | — | 0.5 | 0.2 | 1.0 | — | 30/120 (25) |
| Leaf protoplasts | 1.0 | — | 0.5 | 0.2 | — | 1.0 | 15/20 (75) |
| | 1.0 | — | 0.5 | 0.2 | 1.0 | — | 6/20 (30) |
| | — | 1.0 | 0.5 | 0.2 | — | 1.0 | 26/40 (65) |
| | — | 1.0 | 0.5 | 0.2 | 1.0 | — | 11/40 (28) |

TABLE 8

Effect of Cytokinin on Frequency of Shoot Induction in Callus Derived From VF-36 Tomato Protoplasts

| | Kinetin | Zeatin Riboside | Shoots |
| --- | --- | --- | --- |
| | (Concentration in mg/l) | | Induced/Total |
| Stem Protoplasts | 2.0 | — | 0/80 |
| | — | 1.0 | 7/80 |
| Leaf Protoplasts | 2.0 | — | 0/60 |
| | — | 1.0 | 27/60 |

Other components of the shooting medium were those of TM-4 as previously described except that GA$_3$ at 0.2 mg/l provided in each case.

TABLE 9

| Hormone | Abbreviation |
| --- | --- |
| Auxins | |
| 3-indoleacetic acid | IAA |
| 3-indolebutyric acid | IBA |
| a-naphthaleneacetic acid | NAA |
| Gibberellic acid | GA$_3$ |
| para-chlorophenoxyacetic acid | p-CPA |
| 2,4-dichlorophenoxyacetic acid | 2,4-D |
| Cytokinins | |
| 6-γ,γ-dimethylallylaminopurine | 2iP |
| 6-benzylaminopurine | BAP |
| 6-furfurylaminopurine (kinetin) | Kn |
| Zeatin | Zn |
| Zeatin-Riboside | Zn-R |

What is claimed is:

1. An in vitro method for preconditioning cultivated tomato plants that will be used as sources of protoplast donating plant tissue when extracting protoplasts to be used for regenerating cultivated tomato plants from cultured protoplasts, said in vitro preconditioning method comprising:
    (a) germinating a surface sterilized protoplast donating tomato plant seed, derived from cultivated tomato plants, until a shoot extends from said seed,
    (b) growing said shoot from step (a) in a nutrient medium, to which no exogenous plant hormones have been added, until said shoot develops into a small tomato plantlet having expanded leaves and a substantial stem,
    (c) exposing said tomato plantlet from step (b) to total darkness,
    (d) excising tissue from said tomato plantlet of step (c),
    (e) treating said excised tomato plant tissue of step (d) with "pre-enzyme treatment" (PET) solution, said PET solution being comprised essentially of an osmoticum to which exogenous plant hormones have been added, and
    (f) using said excised, tomato plant tissue from step (e) as a source of protoplast donating tomato plant tissue when extracting protoplasts to be used for regenerating cultivated tomato plants from cultured tomato protoplasts.

2. A method according to claim 1 wherein said cultivated tomato plants are Lycopersicon esculentum tomato plants.

3. A method according to claim 2 wherein said Lycopersicon esculentum tomato plants are Lycopersicon esculentum cultivars selected from the group comprised of Lycopersicon esculentum cv. Red Cherry, Lycopersicon esculentum cv. Cocktail Cherry, Lycopersicon esculentum cv. VFNT Cherry, Lycopersicon esculentum cv. VF36, Lycopersicon esculentum cv. Manapal, Lycopersicon esculentum cv. Floradade, Lycopersicon esculentum cv. UC82, Lycopersicon esculentum cv. Roma, Lycopersicon esculentum cv. Beefsteak, and Lycopersicon esculentum cv. San Marzano.

4. A method according to claim 1 wherein said protoplast donating cultivated tomato plant seed of step (a) is germinated at about 25° C.

5. A method according to claim 1 wherein said shoot of step (b) is grown at about 25° C., with a photoperiod of about 16 hr/8 hr (light/dark).

6. A method according to claim 1 wherein said tomato plantlet of step (c) is exposed to total darkness for about 48 hours.

7. A method according to claim 6 wherein said tomato plantlet is maintained at about 25° C. while being exposed to total darkness.

8. A method according to claim 1 wherein the excised tomato plant tissue of step (d) is excised tomato plant tissue selected from the group consisting of leaf tissue, stem tissue, cotyledon tissue and root tissue.

9. A method according to claim 1 wherein said pre-enzyme treatment (PET) solution of step (e) contains plant hormones.

10. A method according to claim 9 wherein said plant hormones are plant hormones that encourage cell growth and differentiation.

11. A method according to claim 9 wherein said plant hormones are plant hormones selected from the group consisting of auxins and cytokinins.

12. A method according to claim 1 wherein said excised tomato plant tissue in step (e) is treated with said "pre-enzyme treatment" (PET) solution for about 8–14 hours.

13. A method according to claim 1 wherein said "pre-enzyme treatment" (PET) solution of step (e) is chilled.

14. A method according to claim 13 wherein said chilled "pre-enzyme treatment" (PET) solution is chilled to about 10° C.

15. An improved method for regenerating cultivated tomato plants from cultured tomato protoplasts, said regeneration method including the steps of:
    (1) isolating tomato protoplasts from protoplast donating tomato plant tissue derived from cultivated tomato plants,
    (2) culturing said protoplasts from step (1), in growth media containing plant hormones that encourage cell growth, until said protoplasts divide and form small multi-cellular colonies composed of about 100 protoplast-derived cells growing in close proximity to one another, said small multi-cellular colonies not being visible to the naked eye,
    (3) culturing said small multi-cellular colonies from step (2), in growth media containing plant hormones that encourage cell growth, until said small multi-cellular colonies from small mini-calli that are about 3–5 mm in diameter, and visible to the naked eye,
    (4) culturing said small mini-calli from step (3), in differentiation media containing plant hormones that encourage differentiation and further growth, for about one week,
    (5) culturing the calli from step (4) in differentiation media, containing plant hormones that encourage further differentiation and growth of said calli, until shoots grow from said calli,
    (6) removing said shoots from said shoot-bearing differentiated calli of step (5),
    (7) culturing said shoots from step (6), in growth media containing plant hormones that encourage root formation, until said shoots develop roots, and (8) growing said rooted shoots from step (7) until said rooted shoots become tomato plants;

wherein the improvement comprises an in vitro method for preconditioning a protoplast donating cultivated tomato plant prior to protoplast isolation, said in vitro preconditioning method comprising:

(a) germinating a surface sterilized protoplast donating tomato plant seed, derived from cultivated tomato plants, until a shoot extends from said seed, (b) growing said shoot from step (a) in a nutrient medium, to which no exogenous plant hormones have been added, until said shoot develops into a small tomato plantlet having expanded leaves and a substantial stem, exposing said tomato plantlet from step (b) to total darkness, (d) excising tissue from said tomato plantlet of step (c), (e) treating said excised tomato plant tissue of step (d) with "pre-enzyme treatment" (PET) solution, being comprised essentially of an osmoticum to which exogenous auxin and cytokinin plant hormones have been added, and (f) using said excised, tomato plant tissue from step (e) as a source of protoplast donating tomato plant tissue when extracting protoplasts to be used for regenerating cultivated tomato plants from cultured tomato protoplasts.

16. A method according to claim 15 wherein said cultivated tomato plants are *Lycopersicon esculentum* tomato plants.

17. A method according to claim 16 wherein said *Lycopersicon esculentum* tomato plants are *Lycopersicon esculentum* cultivars selected from the group comprised of *Lycopersicon esculentum* cv. Red Cherry, *Lycopersicon esculentum* cv. Cocktail Cherry, *Lycopersicon esculentum* cv. VFNT Cherry, *Lycopersicon esculentum* cv. VF36, *Lycopersicon esculentum* cv. Manapal, *Lycopersicon esculentum* cv. Floradade, *Lycopersicon esculentum* cv. UC82, *Lycopersicon esculentum* cv. Roma, *Lycopersicon esculentum* cv. Beefsteak, and *Lycopersicon esculentum* cv. San Marzano.

18. A method according to claim 15 wherein said protoplast donating cultivated tomato plant seed of step (a) is germinated at about 25° C.

19. A method according to claim 15 wherein said shoot of step (b) is grown at about 25° C., with a photoperiod of about 16 hr/8 hr (light/dark).

20. A method according to claim 15 wherein said tomato plantlet of step (c) is exposed to total darkness for about 48 hours.

21. A method according to claim 20 wherein said tomato plantlet is maintained at about 25° C. while being exposed to total darkness.

22. A method according to claim 15 wherein the excised tomato plant tissue of step (d) is excised tomato plant tissue selected from the group consisting of leaf tissue, stem tissue, cotyledon tissue and root tissue.

23. A method according to claim 15 wherein said pre-enzyme treatment (PET) solution of step (e) contains plant hormones.

24. A method according to claim 23 wherein said plant hormones are plant hormones that encourage cell growth and differentiation.

25. A method according to claim 23 wherein said plant hormones are plant hormones selected from the group consisting of auxins and cytokinins.

26. A method according to claim 15 wherein said excised tomato plant tissue in step (e) is treated with said "pre-enzyme treatment" (PET) solution for about 8-14 hours.

27. A method according to claim 15 wherein said "pre-enzyme treatment" (PET) solution of step (e) is chilled.

28. A method according to claim 27 wherein said chilled "pre-enzyme treatment" (PET) solution is chilled to about 10° C.

29. An in vitro method for preconditioning cultivated tomato plants that will be used as sources of protoplast donating plant tissue when extracting protoplasts to be used for regenerating cultivated tomato plants from cultured protoplasts, said in vitro preconditioning method comprising:

(a) germinating a surface sterilized protoplast donating tomato plant seed, derived from cultivated tomato plants, in sterilized water, at about 25° C., until a shoot extends from said seed, (b) growing said shoot from step (a) in a soil free nutrient medium, to which no exogenous plant hormones have been added, said shoot being grown at about 25° C., with a photoperiod of about 16 hr/8 hr (light/dark), until said shoot develops into a small tomato plantlet having expanded leaves and a substantial stem, (c) exposing said tomato plantlet from step (b) to total darkness, for about 48 hours, while maintaining said tomato plantlet at about 25° C., (d) excising tissue from said tomato plantlet of step (c), (e) treating said excised tomato plant tissue of step (d) with a chilled "pre-enzyme treatment" (PET) solution, for about 8 hours to about 14 hours, said "pre-enzyme treatment" (PET) solution being comprised essentially of an osmoticum to which exogenous auxin and cytokinin plant hormones have been added, (f) using said excised, treated tomato plant tissue from step (e) as a source of protoplast donating tomato plant tissue when extracting protoplasts to be used for regenerating cultivated tomato plants from cultured tomato protoplasts.

30. A method according to claim 29 wherein said cultivated tomato plants are *Lycopersicon esculentum* tomato plants.

31. A method according to claim 30 wherein said *Lycopersicon esculentum* tomato plants are *Lycopersicon esculentum* cultivars selected from the group comprised of *Lycopersicon esculentum* cv. Red Cherry, *Lycopersicon esculentum* cv. Cocktail Cherry, *Lycopersicon esculentum* cv. VFNT Cherry, *Lycopersicon esculentum* cv. VF36, *Lycopersicon esculentum* cv. Manapal, *Lycopersicon esculentum* cv. Floradade, *Lycopersicon esculentum* cv. UC82, *Lycopersicon esculentum* cv. Roma, *Lycopersicon esculentum* cv. Beefsteak, and *Lycopersicon esculentum* cv. San Marzano.

32. A method according to claim 29 wherein the excised tomato plant tissue of step (d) is excised tomato plant tissue selected from the group consisting of leaf tissue, stem tissue, cotyledon tissue and root tissue.

33. A method according to claim 29 wherein said chilled "pre-enzyme treatment" (PET) solution from step (e) is chilled to about 10° C.

34. An improved method for regenerating cultivated tomato plants from cultured tomato protoplasts, said regeneration method including the steps of:

(1) isolating tomato protoplasts from protoplast donating tomato plant tissue derived from cultivated tomato plants, (2) culturing said protoplasts from step (1), in growth media containing plant hormones that encourage cell growth, until said protoplasts divide and form small multi-cellular colonies composed of about 100 protoplast-derived cells growing in close proximity to one another, said small multi-cellular colonies not being visible to the naked eye, (3) culturing said small multi-cellular colonies from step (2), in growth media containing plant hormones that encourage cell growth, until said small multi-cellular colonies form small mini-calli that are about 3-5 mm in diameter, and visible to the naked eye, (4) culturing said small mini-calli from step (3), in differentiation media containing plant hormones that encourage differentiation and further growth, for about one week, (5) culturing the calli from step (4) in differentiation media, containing plant hormones that encourage further differentiation and growth of said calli, until shoots grow from said calli, (6) removing said shoots from said shoot-bearing differentiated calli of step (5), (7) culturing said shoots from step (6), in growth media containing plant hormones that encourage root formation, until said shoots develop roots, and (8) growing said rooted shoots from step (7) until said rooted shoots become tomato plants;

wherein the improvement comprises an in vitro method for preconditioning a protoplast donating cultivated tomato plant prior to protoplast isolation, said in vitro preconditioning method comprising:

(a) germinating a surface sterilized protoplast donating tomato plant seed, derived from a cultivated tomato plant, in sterilized water, at about 25° C., until a shoot extends from said seed, (b) growing said shoot from step (a) in a soil free nutrient medium, to which no exogenous plant hormones have been added, said shoot being grown at about 25° C., with a photoperiod of about 16 hr/8 hr (light/dark), until said shoot develops into a small tomato plantlet having expanded leaves and a substantial stem, (c) exposing said tomato plantlet from step (b) to total darkness for about 48 hours, while maintaining said tomato plantlet at about 25° C., (d) excising tissue from said tomato plantlet of step (c), (e) treating said excised tomato plant tissue of step (d) with a chilled "pre-enzyme treatment" (PET) solution, for about 8 hours to about 14 hours, said PET solution being comprised essentially of an osmoticum to which exogenous auxin and cytokinin plant hormones have been added, (f) using said excised, treated tomato plant tissue from step (e) as protoplast donating tomato plant tissue for protoplast isolation.

35. A method according to claim 34 wherein said cultivated tomato plants are *Lycopersicon esculentum* tomato plants.

36. A method according to claim 34 wherein said *Lycopersicon esculentum* tomato plants are *Lycopersicon esculentum* cultivars selected from the group comprised of *Lycopersicon esculentum* cv. Red Cherry, *Lycopersicon esculentum* cv. Cocktail Cherry, *Lycospersicon esculentum* cv. VFNT Cherry, *Lycopersicon esculentum* cv. VF36, *Lycopersicon esculentum* cv. Manapal, *Lycopersicon esculentum* cv. Floradade, *Lycopersicon esculentum* cv. UC82, *Lycopersicon esculentum* cv. Roma, *Lycopersicon esculentum* cv. Beefsteak, and *Lycopersicon esculentum* cv. San Marzano.

37. A method according to claim 34 wherein the excised plant tissue in step (d) is excised plant tissue selected from the group consisting of leaf tissue, stem tissue, cotyledon tissue and root tissue.

38. A method according to claim 34 wherein said chilled "pre-enzyme treatment" (PET) solution from step (e) is chilled to about 10° C.

39. An in vitro method for preconditioning *Lycopersicon esculentum* tomato plants that will be used as sources of protoplast donating plant tissue when extracting protoplasts to be used for regenerating *Lycopersicon esculentum* tomato plants from cultured protoplasts, said in vitro preconditioning method comprising:

(a) germinating a surface sterilized protoplast donating tomato plant seed, derived from cultivated tomato plants, in sterilized water, at about 25° C., until a shoot extends from said seed, (b) growing said shoot from step (a) in a soil free nutrient medium, to which no exogenous plant hormones have been added, said shoot being grown at about 25° C., with a photoperiod of about 16 hr/8 hr (light/dark), until said shoot develops into a small tomato plantlet having expanded leaves and a substantial stem, (c) exposing said tomato plantlet from step (b) to total darkness, for about 48 hours, while maintaining said tomato plantlet at about 25° C., (d) excising tissue from said tomato plantlet of step (c), (e) treating said excised tomato plant tissue of step (d) with a chilled "pre-enzyme treatment" (PET) solution, for about 8 hours to about 14 hours, said "pre-enzyme treatment" (PET) solution being comprised essentially of an osmoticum to which exogenous auxin and cytokinin plant hormones have been added, (f) using said excised, treated tomato plant tissue from step (e) as a source of protoplast donating tomato plant tissue when extracting protoplasts to be used for regenerating cultivated tomato plants from cultured tomato protoplasts.

40. A method according to claim 39 wherein said *Lycopersicon esculentum* tomato plants are *Lycopersicon esculentum* cultivars selected from the group comprised of *Lycopersicon esculentum* cv. Red Cherry, *Lycopersicon esculentum* cv. Cocktail Cherry, *Lycopersicon esculentum* cv. VFNT Cherry, *Lycopersicon esculentum* cv. VF36, *Lycopersicon esculentum* cv. Manapal, *Lycopersicon esculentum* cv. Floradade, *Lycopersicon esculentum* cv. UC82, *Lycopersicon esculentum* cv. Roma, *Lycopersicon esculentum* cv. Beefsteak, and *Lycopersicon esculentum* cv. San Marzano.

41. A method according to claim 39 wherein the excised tomato plant tissue of step (d) is excised tomato plant tissue selected from the group consisting of leaf tissue, stem tissue, cotyledon tissue and root tissue.

42. A method according to claim 39 wherein said chilled "pre-enzyme treatment" (PET) solution from step (e) is chilled to about 10° C.

43. An improved method for regenerating *Lycopersicon esculentum* tomato plants from cultured tomato protoplasts, said regeneration method including the steps of:

(1) isolating tomato protoplasts from protoplast donating tomato plant tissue derived from *Lycopersicon esculentum* tomato plants, (2) culturing said protoplasts from step (1), in growth media containing plant hormones that encourage cell growth, until said protoplasts divide and form small multi-cellular colonies composed of about 100 protoplast-derived cells growing in close proximity to one another, said small multi-cellular colonies not being visible to the naked eye, (3) culturing said small multi-cellular colonies from step (2), in growth media containing plant hormones that encourage cell growth, until said small multi-cellular colonies from small mini-calli that are about 3-5 mm in diameter, and visible to the naked eye, (4) culturing said small mini-calli from step (3), in differentiation media containing plant hormones that encourage differentiation and further growth, for about one week, (5) culturing the calli from step (4) in differentiation media, containing plant hormones that encourage further differentiation and growth of said calli, until shoots grow from said calli, (6) removing said shoots from said shoot-bearing differentiated calli of step (5), (7) culturing said shoots from step (6), in growth media containing plant hormones that encourage root formation, until said shoots develop roots, and (8) growing said rooted shoots from step (7) until said rooted shoots become tomato plants;

wherein the improvement comprises an in vitro method for preconditioning a protoplast donating *Lycopersicon esculentum* tomato plant prior to protoplast isolation, said in vitro preconditioning method comprising:

(a) germinating a surface sterilized protoplast donating tomato plant seed, derived from a *Lycopersicon esculentum* tomato plant, in sterilized water, at about 25° C., until a shoot extends from said seed, (b) growing said shoot from step (a) in a soil free nutrient medium, to which no exogenous plant hormones have been added, said shoot being grown at about 25° C., with a photoperiod of about 16 hr/8 hr (light/dark), until said shoot develops into a small tomato plantlet having expanded leaves and a substantial stem, (c) exposing said tomato plantlet from step (b) to total darkness for about 48 hours, while maintaining said tomato plantlet to about 25° C., (d) excising tissue from said tomato plantlet of step (c), (e) treating said excised tomato plant tissue of step (d) with a chilled "pre-enzyme treatment" (PET) solution, for about 8 hours to about 14 hours, said PET solution being comprised essentially of an osmoticum to which exogenous auxin and cytokinin plant hormones have been added, (f) using said excised, treated tomato plant tissue from step (e) as protoplast donating tomato plant tissue for protoplast isolation.

44. A method according to claim 43 wherein said *Lycopersicon esculentum* tomato plants are *Lycopersicon esculentum* cultivars selected from the group comprised of *Lycopersicon esculentum* cv. Red Cherry, *Lycopersicon esculentum* cv. Cocktail Cherry, *Lycopersicon esculentum* cv. VFNT Cherry, *Lycopersicon esculentum* cv. VF36, *Lycopersicon esculentum* cv. Manapal, *Lycopersicon esculentum* cv. Floradade, *Lycopersicon esculentum* cv. UC82, *Lycopersicon esculentum* cv. Roma, *Lycopersicon esculentum* cv. Beefsteak, and *Lycopersicon esculentum* cv. San Marzano.

45. A method according to claim 43 wherein the excised plant tissue in step (d) is excised plant tissue selected from the group consisting of leaf tissue, stem tissue, cotyledon tissue and root tissue.

46. A method according to claim 43 wherein said chilled "pre-enzyme treatment" (PET) solution from step (e) is chilled to about 10° C.

* * * * *